United States Patent [19]

Lipinski

[11] Patent Number: 5,066,659
[45] Date of Patent: Nov. 19, 1991

[54] SPIRO-HETEROAZALONES FOR TREATMENT OF DIABETIC COMPLICATIONS

[75] Inventor: Christopher A. Lipinski, Waterford, Conn.

[73] Assignee: Pfizer Inc., New York, N.Y.

[21] Appl. No.: 554,952

[22] Filed: Jul. 12, 1990

Related U.S. Application Data

[63] Continuation of Ser. No. 370,143, Jun. 23, 1989, abandoned, which is a continuation of Ser. No. 44,400, filed as PCT/US84/01767 Oct. 30, 1984, published as WO86/02647 May 9, 1986, abandoned.

[51] Int. Cl.$^5$ ............... A61K 31/41; C07D 471/10
[52] U.S. Cl. ................................. 514/278; 546/15
[58] Field of Search ..................... 546/15; 514/278

[56] References Cited

U.S. PATENT DOCUMENTS

| | | | |
|---|---|---|---|
| 4,117,230 | 9/1978 | Sarges | 548/308 |
| 4,147,795 | 4/1979 | Sarges | 546/15 |
| 4,210,756 | 7/1980 | Sarges | 546/15 |
| 4,282,229 | 8/1981 | Sarges | 548/309 |
| 4,283,409 | 8/1981 | Belletire et al. | 546/15 |
| 4,540,704 | 9/1985 | Ueda et al. | 548/309 |

*Primary Examiner*—Robert T. Bond
*Attorney, Agent, or Firm*—Peter C. Richardson; Paul H. Ginsburg; Robert F. Sheyka

[57] ABSTRACT

Spiro-heteroazolones are disclosed which are useful as aldose reductase inhibitors and as therapeutic agents for the treatment of complications arising from diabetes. Pharmaceutical compositions containing the spiro compounds and a method of treating diabetic complications are also disclosed.

3 Claims, No Drawings

SPIRO-HETEROAZALONES FOR TREATMENT OF DIABETIC COMPLICATIONS

This is a continuation of application Ser. No. 370,143, filed on June 23, 1989 which is a continuation of application Ser. No. 044,400, filed as PCT/US84/01767 Oct 30, 1984, published as WO86/02647 May 9, 1986 both abandoned.

Technical Field

This invention relates to novel spiro-heteroazolones useful in the treatment of certain chronic complications arising from diabetes mellitus, such as diabetic cataracts, retinopathy and neuropathy, to pharmaceutical compositions containing such compounds and to a method of using these compounds.

Background Art

In the past various attempts have been made to obtain more effective oral anti-diabetic agents. Generally, these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e] isoquinoline-2(3H)-acetic acid and derivatives thereof to be useful for the treatment of these conditions. U.S. Pat. No. 4,117,230 teaches the use of certain hydantoins for treating complications of diabetes as aldose reductase inhibitors. Such aldose reductase inhibitors function by inhibiting the activity of the enzyme aldose reductase, which is primarily responsible for regulating the reduction of aldoses, such as glucose and galactose, to the corresponding polyols, such as sorbitol and galactitol, in humans and other animals. In this way unwanted accumulations of galactitol in the lens of galactosemic subjects and of sorbitol in the lens, or peripheral nervous cord and kidneys of various diabetic subjects are prevented or reduced. Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

Carr et al., U.S. Pat. No. 3,985,888, teach certain spiroalkanone-imides and their use as sedatives. European Patent Application Publication No. 0065392 discloses certain spiro-succinimide derivatives and their use as aldose reductase inhibitors.

Disclosure of Invention

The compounds of the present invention are spiroheteroazolones of the formula

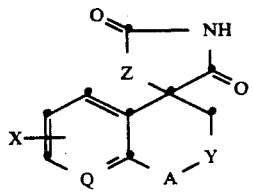

I or a pharmaceutically acceptable salt thereof, wherein A is methylene, hydroxymethylene, or methine; Y is methylene, alkylmethylene, methine or alkylmethine, wherein alkyl in each instance has 1-4 carbon atoms; with the proviso that when A is methine, Y is methine or alkylmethine;

Z is oxygen, sulfur, or nitrogen substituted by hydrogen;

Q is nitrogen or nitrogen-N-oxide; and X is in the 3' position and is hydrogen, halo, alkyl, alkoxy having 1-4 carbon atoms, alkylthio, alkylsulfinyl, alkylsulfonyl, phenoxy, phenylthio, or nitro; or X is in the 2'-position and is hydrogen, alkyl or alkoxy having 1-4 carbon atoms; wherein alkyl in each instance has 1-4 carbon atoms; with the proviso that when Q is nitrogen-N-oxide, X is not alkylthio, alkylsufinyl or phenylthio.

Preferred compounds include those wherein Z is nitrogen substituted by hydrogen, and Q is nitrogen or nitrogen-N-oxide. Further preferred are compounds wherein Y is methylmethylene, A is methylene or hydroxymethylene and X is hydrogen or chloro. Also preferred are compounds wherein A is methine, Y is methylmethine and X is hydrogen.

Both mixtures of optically active isomers and partially or completely optically resolved isomers of the compounds claimed herein are within the scope of the present invention.

Also embraced by the present invention are pharmaceutical compositions comprising a pharmaceutically acceptable carrier or diluent and a compound of formula I. The present invention further comprises a method of treating a diabetic host for diabetes-associated complications which comprises administering to the host an effective amount of a compound of formula I.

Detailed Description

The numbering system of the spiro compounds of formula I is as shown.

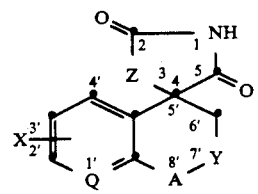

The compounds are spiro[imidazolidine, oxazolidine or thiazolidine-4,5'(6'H)-quinoline or quinoline-N-oxide)]2,5-diones. The compounds can be substituted by X in the 2' or 3' positions and can be 7',8'-dihydro derivatives. Diastereomers can be separated by methods known in the art such as recrystallization with a suitable solvent such as isopropanol, or trituration, for example, with an alcohol-ether solvent such as isopropanol-diethyl ether. The terms "Rel" and "(±)" each mean a 1:1 racemic mixture of the two optically active enantiomers.

When X is halo, halo includes fluoro, chloro, bromo and iodo.

In the Synthetic Scheme a preparation of compounds of formula I is shown. Compounds of formulae IA-D are subclasses of compounds of formula I and are within the scope of the present invention. Starting diketone II wherein R is hydrogen or alkyl having 1-4 carbon atoms is reacted with ammonia in a refluxing solvent, such as benzene, which will remove the water of reaction as an azeotrope to obtain ketone eneamine III. When X is hydrogen, III is reacted with propynal in a polar aprotic organic solvent such as dimethylformamide at an initial temperature of between about -10° and 25° C., preferably about 0° C., followed by a period of heating of between about 15 and 90 minutes, preferably about 45 minutes, at a temperature of between about 100° and 153° C., preferably about 153° C., to obtain tetrahydroquinoline derivative IV where X is hydrogen.

When X is other than hydrogen, alkene aldehyde, V or VI, which are known compounds or can be prepared analogously to the known compounds, is reacted with ketone eneamine III in a polar, aprotic organic solvent such as dimethylformamide at between about −10° and 25° C., followed by heating at between about 100° and 153° C., to obtain tetrahydroquinoline derivative IV.

SYNTHETIC SCHEME

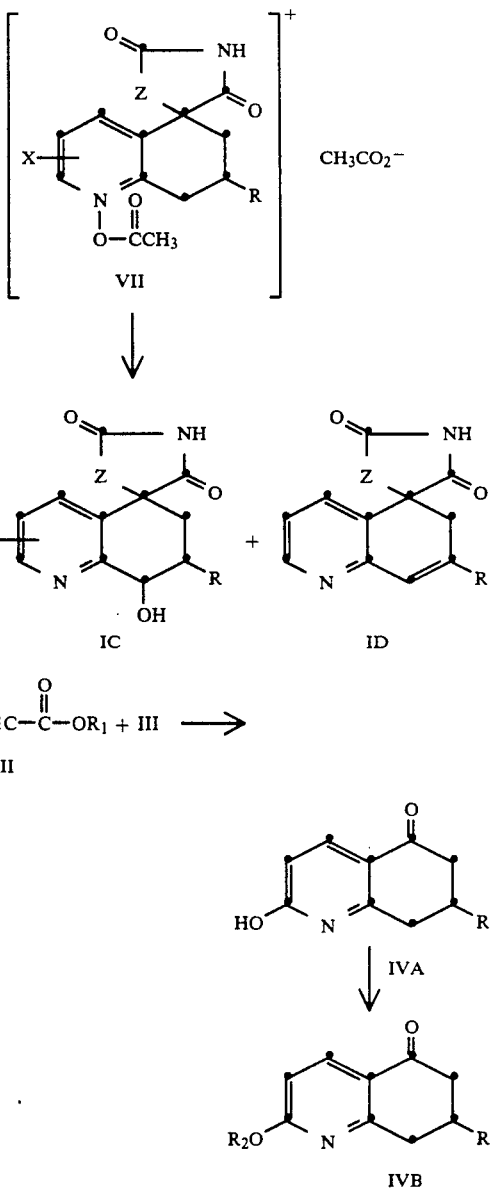

When Z is nitrogen substituted with hydrogen, the compound of formula IV can be reacted to obtain the corresponding compounds of formula IA, for example, by means of the methods described in U.S. Pat. No. 4.,117,230. A compound of formula IV is condensed with an alkali metal cyanide (e.g., sodium cyanide or potassium cyanide) and ammonium carbonate to form the desired spiro-hydantoin final product. This reaction is normally carried out in the presence of a reaction-inert polar organic solvent medium in which both the reactants and reagents are mutually miscible. Preferred organic solvents include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diet,hylformamide and N,N-dimethylacetamide, etc. In general, the reaction is conducted at a temperature that is in the range of from about 20° C. to about 120° C. for a period of about two hours to about four days. Although the amount of reactant and reagents employed in the reaction can vary to some extent, it is preferable to employ at least a slight molar excess of the alkali metal cyanide reagent with respect to the carbonyl ring compound starting material in order to effect maximum yield. Upon completion of the reaction, the desired product is easily isolated in a conventional manner, e.g., by first diluting the reaction mixture with water (boiling if necessary) and then cooling the resultant aqueous solution to room temperature, followed by acidification to afford the spiro-hydantoin compound in the form of a readily-recoverable precipitate.

When X is 2'-alkoxy, the preferred method of preparing the corresponding compounds of formula I is according to the procedure of Dubas-Sluyter et al., *Recueil Chim Pays Bas*, 91, 157–160 (1972) wherein a compound of formula III is reacted with an alkyl propiolate VIII wherein $R_1$ is alkyl having 1–4 carbon atoms, preferably methyl, in a polar aprotic solvent such as dimethylformamide or carbitol at a temperature range of between about 100° and 153° C., preferably about 153° C., to obtain the hydroxy compound of formula IVA. It is to be understood that the compound of IVA may also be present as the 2-pyridone isomer.

The compound of formula IVA is reacted with an a water soluble inorganic silver salt such as silver nitrate and aqueous base such as potassium hydroxide at a pH of between about 9 and 12, preferably about 10.5, and at a temperature of between about 0° and 60° C., preferably about 25° C., to form a silver salt. The isolated silver salt is reacted with an alkyl iodide of the formula $R_2$-I wherein $R_2$ is alkyl having 1–4 carbon atoms at a temperature of between about 25° and 100° C., preferably 60° C., to obtain the 2-alkoxy quinoline derivative IVB. The conversion to compounds of formula I continues according to the procedures for, a compound of formula IV.

When Z is oxygen, the compound of formula IV can be reacted to obtain the corresponding compounds of formula IA by means of the methods described, for example, in U.S. Pat. Nos. 4,226,875 and 4,267,342. In one procedure, a compound of formula IV is reacted with a trialkylsilyl cyanide, wherein each alkyl has 1–4 carbon atoms and is preferably methyl, to form the corresponding cyano trialkylsilyloxy derivative. The reaction is conducted in the presence of a Lewis acid catalyst, such as a zinc halide, aluminum halide or boron trifluoride, with zinc iodide being a preferred catalyst. Temperatures in the range of about 0° C. to about 50° C. are generally employed, preferably about 0° C. to 20° C., in an inert organic solvent, typically an ether such as diethyl ether, dimethoxyethane, tetrahydrofuran, dioxane and the like, or a halohydrocarbon such as methylene chloride, chloroform and similar solvents. The resulting cyano trialkylsilyloxy derivative is then converted to an alkyl-hydroxycarboximidate derivative by reaction with an acid in an alcohol solvent $R_4OH$. Suitable acids include hydrogen halides, especially hydrogen chloride. The alcohol $R_4OH$ may be either a lower alkanol of 1 to 4 carbon atoms, benzyl alcohol or a substituted benzyl alcohol, the substituent including chloro, bromo, fluoro, hydroxy, alkyl of 1 to 3 carbon atoms and alkoxy of 1 to 3 carbon atoms. The reaction is generally conducted at temperatures in the range of about −10° C. to about 25° C., preferably at about 0° C. to 10° C.

The hydroxy carboximidate derivative may be converted directly to the desired spiro-oxazolidin-2,5dione IA by a number of methods. In all cases, a spiro4-alkoxy oxazolin-2-one is an intermediate and can, if desired, be isolated from the reaction mixture. However, it is generally preferred to convert directly without such isolation of the intermediate. The hydroxy carboximidate may be reacted with phosgene in the presence of a base such as triethylamine, or other trialkylamines having from 1 to 4 carbon atoms in each alkyl group, in an inert organic solvent such as an ether, for example, diethyl ether, tetrahydrofuran, dimethoxyethane, dioxane and the like. The phosgene is generally bubbled through the reaction solution at a temperature of about −10° C. to about 10° C., for about to 15 minutes and the solution is subsequently stirred about 20° C. to 50° C., preferably at about 25° C. for about 12 to 48 hours, when the spiro-oxazolin-2-one is predominantly formed. This intermediate may then be converted to the desired spiro oxazolidin-2,5-dione IA either by a further perfusion of phosgene at about −10° C. to about 10° C. for about 15 to 75 minutes, followed by stirring at room temperature for a further period of about 12 to 48 hours. Alternatively, an alkali metal carbonate, such as potassium or sodium carbonate, or ammonium carbonate can be added to a solution of the 15 intermediate in, for example, aqueous tetrahydrofuran, and stirred at a temperature of about 15° C. to about = C., preferably at about 25° C., for a period of about 6 to 24 hours to form the desired spirooxazolidin-2, 5-dione IA.

The desired spiro-oxazolidin-2,5-dione IA can also be prepared from the hydroxy carboximidate derivative by reaction with an alkyl haloformate, where the alkyl group is of 1 to 4 carbon atoms, a preferred reagent being ethyl chloroformate. The reaction is generally conducted by stirring the hydroxy carboximidate intermediate together with the alkyl haloformate in an inert solvent, such as pyridine, at a temperature of about −10° C. to about 15° C., preferably at about 0° C. for a period of 30 minutes to about 2 hours, followed by heating the solution to a higher temperature, about 50° C. to about 150° C., preferably about 90° C. to 120° C., for example, to reflux temperature in pyridine, for about 2 to about 6 hours. If desired the spiro-oxazolidin-2-one intermediate can be isolated from the initial reaction mixture after heating the solution for relatively shorter periods, for example about 1 hour.

The spiro-oxazolidin-2,5-diones can also be prepared from the hydroxy carboximidate derivative by reaction with 1,1'-carbonyl-diimidazole, the reaction being generally conducted at a temperature of about 50° C. to 150° C., preferably about 80° C. to 110° C., neat or in an inert organic solvent such as dioxane, tetrahydrofuran, dimethoxyethane, diethyl ether and the like, for a period of about 12 to 36 hours. If desired, the intermediate spiro-oxazolin-2-one can be obtained by heating for only a relatively short period of time, for example, about 30 minutes to about 90 minutes.

When Z is sulfur, the compounds of formula IA can be prepared by taking advantage of the hydroxy carboximidate derivatives previously discussed. These are converted to chlorocarboximidate derivatives by heating with thionyl chloride at between about 35° C. and the reflux temperature of about 79° C. for 1-3 hours, preferably about 2 hours. The resulting chlorocarboximate derivatives are reacted with thiourea in a refluxing alkanol of 1-4 carbons, preferably ethanol, for about 15-90 minutes, preferably 30 minutes, followed by a brief aqueous hydrolysis either during column chromatography on acidic silica gel, or in aqueous tetrahydrofuran or dioxane containing about 0.1 to 6N hydrochloric acid at about 0°-60° C., preferably about 25° C.

The compound of formula IA can be oxidized to the compound of formula IB wherein Q is nitrogen -N-oxide by any procedure known in the art. In one procedure, about 30 percent by volume aqueous hydrogen peroxide in an acidic solvent such as acetic acid at a temperature of between about 0° and 100° C., preferably about 85° C. This oxidation procedure should be avoided when X is alkylthio, alkylsulfinyl or phenylthio in order to prevent oxidation of the sulfur moiety on X.

The compound of formula IB can be transformed into a compound of formula IC or ID by the reaction with acetic anhydride in acetic acid or neat containing a trace of water at a temperature range of between about 60° and 95° C., preferably about 95° C.

The resulting acetate salt VII is reacted at about 0°-60° C., preferably about 25° C., in an aqueous solvent such as water, aqueous tetrahydrofuran or aqueous dioxane at a pH of between about 10 and 14, preferably about 13, to obtain IC and ID. The hydroxide aqueous solution relative amounts formed of these product depends upon the reaction temperature, pH and nature of the R substituent.

Because of the acidic hydrogen atom in the spiro 5-membered heterocyclic ring of the compounds of formula I, salts may be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired cation and evaporated the solution subsequently to dryness. Suitable pharmaceutically acceptable cations for this purpose include, but are not limited to, alkali metal cations such as potassium and sodium, ammonium or water soluble amine addition salts such as the lower alkanolammonium and other base salts with organic amines which are pharmaceutically acceptable and alkaline earth metal cations such as calcium and magnesium.

Acid addition salts can be formed for compounds of formula I when Q is nitrogen. Suitable salts include those derived from hydrochloric acid, sulfuric acid or methylsulfonic acid. These acid addition salts can be prepared by the addition of the appropriate strong acid to a lower alcoholic solution of a compound of formula I at a temperature of 0°-60° C., preferably 25° C., followed by concentration to obtain the desired product. Alternatively, an aqueous slurry of a compound of formula I can be mixed with the appropriate strong acid at about 0° -60° C., preferably about 25° C., followed by freeze drying and recrystallization from a lower alcohol.

Pharmaceutically acceptable salts are those which do not cause unacceptable adverse reactions when administered.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention and alleviation of such conditions.

The compound may be administered to a subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. per day. However, some variation in dosage will necessarily occur depending on the condition of the subject being treated. The person responsible for administration will, in any event, determine the appropriate.. dose for the individual subject.

The novel compounds of the invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral adminstration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal adminsitration. In this connection, the sterile aqueous media employed are all readily available by standard techniques known to those skilled in the art.

Compounds of formula I may not only be advantageously employed for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula I, or a pharmaceutically acceptable salt thereof, in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potasssium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium !chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve and lens of acutely streptozotocinized, i.e. diabetic, rats; (3) measuring their ability to reverse already-elevated sorbitol levels in the sciatic nerve and lens of chronic streptozotocin-induced diabetic rats; (4) measuring their ability to prevent or inhibit galacticol formation in the lens of acutely galactosemic rats; (5) measuring their ability to delay cataract formation and reduce the severity of lens opacities in chronic galactosemic rats; (6) measuring their ability to prevent sorbitol accumulation and cataract formation in isolated rat lens incubated with glucose; and (7) measuring their ability to reduce already elevated sorbitol levels in isolated rat lens incubated with glucose.

The present invention is illustrated by the following examples. It will be understood, however, that the invention is not limited to the specific details of these examples. Proton nuclear magnetic resonance spectra (NMR) were measured at 250 MHz (unless otherwise indicated) for solutions in perdeuterodimethyl sulfoxide (DMSO-$d_6$) and peak positions are expressed in parts per million (ppm) downfield from tetramethylsilane. The peak shapes are denoted as follows: s, singlet; d, doublet; t, triplet; q, quartet; m, multiplet; b, broad; very, v.

EXAMPLE 1 rel 4,5'S 7'R
Spiro[imidazolidine-4,5'(6'H)-quinoline]2,5'-dione
7',8'-dihydro-7'-methyl To a solution of 13.3 g (0.138 mol) of ammonium carbonate and 3.8 g (0.058 mol) potassium cyanide in 53 ml water was added a solution of 4.75 g (0.029 mol) 7-methyl, 7,8-dihydro-quinolin-5(6H)-one in 53 ml ethanol. The reaction was heated at 65° C for 72 hours. The solution was cooled and filtered and the filtrate was brought to pH 6.5 at which point a gummy solid precipitated. The solid was filtered and washed well with water. Recrystallization from ethanol gave 2.0 g of the title compound: mp. 252-254° C. as a mixture composed of 80% of the rel 7'R methyl diastereomer and 20% of the rel 7'S methyl diastereomer. NMR DMSO-6): 11.03 (vbs, 1H); 8.76 (s, 0.8×1H); 8.47 (m, 1H); 8.36 (s, 0.2×1H); 7.68 (m, 0.2×1H); 7.46 (m, 0.8×1H); 7.27 (m, 1H); 2.85-3.0 (m, 1H); 2.35-2.6 (m, 1H); 2.0-2.2 (m, 1H); 1.75-2.0 (m, 0.8×1H); 1.64 (t, 0.2×1H); 1.09 (d, 0.8×3H); and 1.05 (d, 0.2×3H) ppm.

EXAMPLE 2 rel, 4,5'S 7'S
Spiro[imidazolidine-4,5'(6'H)-quinoline]-2,5-dione-7',8'-dihydro-7'-methyl Concentration of the ethanol mother liquors from preparation of material enriched in the rel 4,5'S 7'R diastereomer of Example 1 and recrystallization from ethyl acetate gave 1.45 g of material which was recrystallized from water to give 860 mg of rel 4,5'S 7'S spiro[imidazolidine-4,5'(6'H)-quinoline]-2,5-dione-7',8'-dihydro-7-methyl: mp 145-152° C. as a mixture of 90% rel 7'S methyl diastereomer and 10% rel 7'R methyl diastereomer. NMR (DMSO-$d_6$) 10.88 (vb s, 1H); 8.76 (0. ×1H); 8.5 (m,1H); 8.36 (s, 0.9×1H); 7.68 (m, 0.9×1H); 7.46 (m, 0.×1H); 7.27 (m, 1H); 2.9-3.05 (m,1H); 2.5-2.75 (m, 1H); 2.35-2.5 (m,1H); 2.05-2.15 (b d, 1H); 1.75-1.95 (m, 0.1×1H); 1.64 (t, 0.9×1H), 1.09 (d, 0.1×3H); and 1.05 (d, 0.9×3H) ppm.

EXAMPLE 3 rel 4,5'S 7'R
Spiro[imidazolidine-4,5'(6'H)-quinoline]2,5-dione-7',8'-dihydro-7'-methyl-1'-oxide 1.0 g (4.32 mmol) of a 65:35 diastereomer mixture of rel 4,5'S 7'R and 4,5'S 7'S spiro[imidazolidine-4,5'(6'H)-quinoline]-2,5-dione-7',8'-dihydro-7'-methyl was dissolved in a solution of 0.72 ml (7.0 mmol) of 30 percent hydrogen peroxide in 3.0 ml glacial acetic acid and was heated at 85° C for 15 hours. A test for peroxide with potassium iodide-starch test paper showed no peroxide present. The reaction was concentrated in vacuo to an orange foam which was triturated witn an ethyl acetate, diethyl ether, methanol mixture to afford a tan colored solid amounting to 650 mg: mp 185-195° C. of a 75:25 mixture of the 4,5'S 7'R to 4,5'S 7'S diastereomers.

NMR (DMSO-d$_6$) 8.8 (b s, 1H); 8.32 (m, 1H); 7.35 (m, 1H); 7.1 (m, 1H); 3.05-3.35 (m, H); 1.8-2.6 (m, H); 1.15 (d, 0.75×3H); and 1.10 (d, 0.25×3H) ppm.

EXAMPLE 4 rel 4,5'S 7'S
Spiro[imidazolidine-4,5'(6'H)-quinoline]2,5-dione-7',8'-dihydro-7'-methyl-1'-oxide Concentration of mother liquors from precipitation of the rel 4,5'S 7'R diastereomer of Example 3 and trituration with one-to-one diethyl ether-hexane gave 60 mg of a 70:30 mixture of the 4,5'S-7'S to 4,5'S- 7'R diastereomers: mp 261-264° C. NMR (DMSO-d$_6$) 8.82 (s, 0.3×1H); 8.46 (s, 0.7×1H); 8.3 (t, 1H); 7.35 (d, 0.7×1H); 7.1 (d; 0.3×1H); 3.05-3.35 (m,2H); 1.5-2.3 (m, 3H): 1.15 (d, 0.3×3H); and 1.0 (d, 0.7×3H) ppm.

EXAMPLE 5 rel 4,5'S 7'S, 8'R
Spiro[imidazolidine-4,5'(6'H)-quinoline]-2,5-dione-7',8'-dihydro-8'-hydroxy-7'-methyl 2.7 g (11.68 mmol) of a 65:35 diastereomer mixture of rel 4,5'S 7'R and 4,5'S 7'S spiro[imidazolidine-4,5'(6'H)-quinoline]-2,5-dione-7',8'-dihydro-7'-methyl was dissolved in a solution of 2.11 ml (20.5 mmol) of 30 percent hydrogen peroxide in 8.1 ml glacial acetic acid and was heated at 90° C. for 17 hours. A test for peroxide with potassium iodide-starch paper showed no peroxide present. The reaction was concentrated in vacuo to a yellow oil. Trituration with ethanol gave 3.35 g of a yellow foam after the solvent was removed in vacuo. To the foam (3.33 g) was added 14 ml acetic anhydride plus 2 drops of water and the reaction was stirred at 95° C for 20 min to give a clear yellow solution. The reaction was concentrated in vacuo, ethanol was added and was reconcentrated in vacuo. Repetition of this procedure gave 3.8 g of a tan foam, which was slurried in 100 ml water and a 5 percent aqueous sodium hydroxide solution was added. The reaction mixture was stirred until a clear solution resulted. Thin layer chromatographic analysis (20% methanol, 80% chloroform eluent) on silica gel plates showed the appearance of four new more polar spots visible using 254 nanometer ultraviolet light. The solution was neutralized with concentrated hydrochloric acid to pH 7, and was extracted with five 100 ml portions ethyl acetate. After drying over anhydrous sodium sulfate, concentration in vacuo gave 1.84 g of a tan foam.

Diastereomer Separation Products were separated by high pressure liquid chromatography using a Dupont 8800 HPLC, Zorbax preparative silica gel column, linear gradient starting from 95:5 methylene chloride-methanol to 85:15 methylene chloride-methanol over 20 min., 20 ml/min flow rate with ultraviolet detection at 254 nanometers 1.33 g of crude product was dissolved in 7 ml of 95:5 methylene chloride-methanol. Injections of 0.5 to 1.0 ml were made. Peaks corresponding to 5 components were isolated which did not correspond to the elution order observed by thin layer chromatographic analysis.

Peak 1 by high pressure liquid chromatography (HPLC) corresponded to the 2nd least polar spot by thin layer chromatography (TLC). Peak 2 by HPLC corresponded to the 3rd least polar spot by TLC. Peak 3 by HPLC corresponded to least polar spot by TLC. Peak 4 by HPLC exhibited retention time identical with the 3rd least polar spot by TLC: Peak 5 by HPLC corresponded to the most polar spot by TLC.

Material corresponding to HPLC peak 1 was recrystallized from methanol to give material with mp 239-242° C. Based on the following nuclear magnetic resonance spectral properties it was identified as rel 4,5'S 7'S, 8'R spiro[imidazolidine-4,5'(6'H)quinoline]-2,5-dione- 7',8'-dihydro-8'-hydroxy-7'methyl. NMR (DMSO-d$_6$): 11.1 (b s, 1H); 8.86 (s, 1H); 8.61 (m, 1H): 7.50 (m, 1H); 7.38 (m,1h); 5.35 (b s, 1H); 4.13 (d, 1H, 8'-H, D$_2$O addition J=7.5Hz); 1.8-2.15 (m, 3H); and 1.15 (d 3H)ppm.

rel 4,5'S 7'R, 8'S
spiro[imidazolidine-4,5'(6'H)quinoline]-2,5-dione-7',8'-dihydro 8'-hydroxy-7-methyl Material corresponding to HPLC peak 2 was recrystallized from diethyl ether-methanol-ethanol mixture to give material with mp 236-239° C. Based on the following nuclear magnetic resonance spectral properties it was identified as the title compound. NMR (DMSO-d$_6$) 10.9 (vb s, 1H); 8.60 (m, 1H); 8.36 (s, 1H); 7.61 (m, 1H); 7.36 (m, 1H); 5.28 (b s, 1H); 4.08 (d, 1H, J =10Hz); 2.5 (m, 1H); 2.1 (d, 1H); 1.87 (t, 1H); and 1.12 (d,3H) ppm.

rel 4,5'S
spiro[imidazolidine-4,5'(6'H)-quinoline]2,5-dione-7'8'-dihydro 8'-hydroxy-7'-methyl Material corresponding to HPLC peak 3 was recrystallized material with mp 252-256° C. Based on the following nuclear magnetic resonance spectral properties it was identifed as the title compound. NMR (DSO-d$_6$): 10.85 (vb s, 1H); 8.55 (m, 1H); 8.47 (s, 1H); 7.37 (s, 1H); 5.42 (m, 1H); 4.44 (b d, 1H, J =2.5Hz); 2.5 (m, 1H); 2.17 (m, 1H); 1.77 (m, 1H); and 0.96 (d, 3H) ppm.

rel 4,5'S 7'S, 8'S
spiro[imidazolidine-4,5'(6'H)-quinoline]2,5-dione-7',8'-dihydro-8'-hydroxy Material corresponding to HPLC peak 5 was recrystallized from diethyl ether to give material with mp 238-241° C. Based on the following nuclear magnetic resonance spectral properites it was identified as the title compound. NMR (DMSO-d$_6$): 11.06 (vb s, 1H); 8.71 (s, 1H); 8.56 (m, 1H); 7.5 (m, 1H); 7.37 (m, 1H); 5.40 (d, 1H); 4.37 (b s, 1H, 8'-H, D20 addition, J =2.5Hz); 2.32 (t, 1H); 2.14 (m, 1H); 1.59 (d, 1H); and 1.06 (d, 3H) ppm.

EXAMPLE 6

Spiro[imidazoline-4,5'(6'H)-quinoline]-2,5-dione 3'-chloro-7',8'-dihydro-7'-methYl To a solution of 28.8 mg (0.44 mmol) of potassium cyanide and 100 mg (1.04 mmol) ammonium carbonate in 4 ml ethanol and 4 ml water was added 40 mg (0.204 mmol) 3-chloro-7-methyl-7,8-dihydroquinolin-5(6H)-one and the reaction was stirred at 65° C. for 24 hours. An additional 101 mg of ammonium carbonate was added and heating was continued for 72 hours. An additional 101 mg of ammonium carbonate and 3 ml ethanol and 2 ml water, was added and heating was continued at 65° C. for 24 hours. An additional 101 mg ammonium carbonate was added and heating was continued for 6 days. The ethanol was removed from the dark reaction solution by concentration in vacuo. The residue was diluted with water and the pH was brought to 7 with aqueous hydrochloric acid and the reaction was extracted with two 50 ml portions ethyl acetate. After drying over anhydrous sodium sulfate the solution was concentrated in vacuo to 30 mg of a dark green solid. High resolution mass spectroscopic analysis confirmed the presence of the title compound. Calculated for $C_{12}H_{12}N_3O_2Cl$ exact mass m/e 265.0619. Found: 265.0624.

PREPARATION

3-Chloro-7-methyl-7,8-dihydroquinolin-5(6H)-one

To 2.14 g (0.018 mol) of 2-chloro-3-dimethylaminoacrolein in 20 ml dimethylformamide was added 2.25 g (0.018 mol) of 3-amino-5-methyl-cyclohex-2-enone. The reaction was heated at reflux for 40 hours. Most of the solvent was removed in vacuo and the residue was triturated with petroleum ether and concentrated in vacuo. This procedure was repeated three times. The resultant amber oil was tritured with 50 ml ethyl acetate and filtered to remove an insoluble black powder. The ethyl acetate mother liquors were concentrated in vacuo to give 1.54 g of a dark brown oil. This material (0.93 g) was subjected to column chromatography on silica gel using ethyl acetate as eluent. Material with $R_f$ of 0.45 was isolated as a brown oil. The material was identified as largely containing the title compound based on the following spectral data. Mass spectrum bar peak m/e 195, ratio 195:197 were 3:1 corresponding to chlorine isotopes. NMR (DMSO-d$_6$): 8.78 (d, 1H, J=2.52Hz); 8.15 (d, 1H, J=2.5 Hz); 2.2-3.2 (m, 5H); and 1.14 (d, 5H) ppm.

I claim:

1. A compound of the formula:

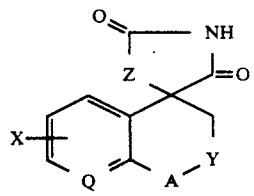

or a pharmaceutically acceptable salt thereof wherein,

A is methylene, hydroxymethylene or methine;

Y is methylene, alkylmethylene, methine, or alkylmethine wherein alkyl in each instance has 1-4 carbon atoms, with the proviso that when A is methine, Y is methine or alkylmethine;

Z is nitrogen substituted by hydrogen;

Q is nitrogen; and

X is in the 3-position and is hydrogen, halo, alkyl, alkoxy having 1-4 carbon atoms alkylthio, alkylsulfinyl, alkylsulfonyl, phenoxy, phenylthio or nitro; or X is in the 2'-position and is hydrogen, alkyl or alkoxy having 1-4 carbon atoms; provided that when X s hydrogen A and Y cannot both be methylene.

2. A pharmaceutical composition compriing a compuund according to claim 1 in an amount feffective for the treatment of diabetes-associated complications and a pharmaceutically acceptable carrier or diluent.

3. A method for treating a diabetes complication in a mammal comprising the step of administering an effective amount of a compound according to claim 1.

* * * * *